(12) United States Patent
Kumar et al.

(10) Patent No.: US 10,201,312 B2
(45) Date of Patent: Feb. 12, 2019

(54) OPPORTUNISTIC MEASUREMENTS AND PROCESSING OF USER'S CONTEXT

(71) Applicant: INTEL CORPORATION, Santa Clara, CA (US)

(72) Inventors: Arvind Kumar, Portland, OR (US); Marisa A. Ahmad, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 642 days.

(21) Appl. No.: 14/563,809

(22) Filed: Dec. 8, 2014

(65) Prior Publication Data

US 2016/0157782 A1 Jun. 9, 2016

(51) Int. Cl.
*A61B 5/02* (2006.01)
*A61B 5/00* (2006.01)
(Continued)

(52) U.S. Cl.
CPC .............. *A61B 5/6897* (2013.01); *A61B 5/02* (2013.01); *A61B 5/0456* (2013.01);
(Continued)

(58) Field of Classification Search
CPC ......... A61B 5/0006; A61B 5/02; A61B 5/021; A61B 5/02125; A61B 5/02416;
(Continued)

(56) References Cited

U.S. PATENT DOCUMENTS 6,059,819 A 5/2000 Weder
2007/0021677 A1 1/2007 Markel
(Continued)

FOREIGN PATENT DOCUMENTS

JP 2005-122339 A 5/2005
KR 10-0755236 B1 9/2007
(Continued)

OTHER PUBLICATIONS

Wang, Ruiping, et al. "Cuff-free blood pressure estimation using pulse transit time and heart rate." Signal Processing (ICSP), 2014 12th International Conference on. IEEE, 2014.*

(Continued)

*Primary Examiner* — Niketa Patel
*Assistant Examiner* — Nathan A Baldwin
(74) *Attorney, Agent, or Firm* — Schwabe, Williamson & Wyatt, P.C.

(57) ABSTRACT

Embodiments of the present disclosure provide techniques and configurations for an apparatus for opportunistic measurements and processing of user's context. In one instance, the apparatus may include a sensor module with sensors disposed on a work surface to maintain direct or indirect contact with portions of user's limbs for a time period when the portions of user's limbs are disposed on the work surface, to obtain readings of first and second parameters of user's context over the time period of the direct or indirect contact; and a processing module to process the readings of the first and second parameters, including to identify a first feature of the first parameter and a second feature of the second parameter that is temporally correlated with the first feature, and determine a third parameter of the user's context based on the identified first and second features. Other embodiments may be described and/or claimed.

13 Claims, 5 Drawing Sheets

(51) Int. Cl.
  *A61B 5/0456* (2006.01)
  *A61B 5/024* (2006.01)
(52) U.S. Cl.
  CPC .......... *A61B 5/6898* (2013.01); *A61B 5/7246* (2013.01); *A61B 5/7267* (2013.01); *A61B 5/02416* (2013.01); *A61B 2560/0462* (2013.01); *A61B 2562/0219* (2013.01)
(58) Field of Classification Search
  CPC ... A61B 5/0402; A61B 5/0404; A61B 5/0456; A61B 5/1455; A61B 5/681; A61B 5/6887; A61B 5/6898; A61B 2560/0468; A61B 2560/0462
  See application file for complete search history.

(56) References Cited

U.S. PATENT DOCUMENTS

| | | | |
|---|---|---|---|
| 2007/0027386 | A1 | 2/2007 | Such et al. |
| 2008/0249382 | A1* | 10/2008 | Oh .................. A61B 5/021 600/324 |
| 2010/0049059 | A1* | 2/2010 | Ha .................. A61B 5/021 600/485 |
| 2010/0056880 | A1 | 3/2010 | Cho et al. |
| 2010/0081946 | A1 | 4/2010 | Garudadri et al. |
| 2010/0174164 | A1 | 7/2010 | Brister et al. |
| 2010/0228136 | A1* | 9/2010 | Keel .................. A61B 5/02416 600/507 |
| 2010/0298658 | A1* | 11/2010 | McCombie ........ A61B 5/02028 600/301 |
| 2010/0324389 | A1* | 12/2010 | Moon .................. A61B 5/746 600/324 |
| 2011/0015496 | A1 | 1/2011 | Sherman et al. |
| 2011/0092780 | A1 | 4/2011 | Zhang et al. |
| 2011/0301436 | A1* | 12/2011 | Teixeira ............... A61B 5/0402 600/301 |
| 2011/0319787 | A1 | 12/2011 | Lamoise et al. |
| 2012/0006147 | A1 | 1/2012 | Sano |
| 2012/0022385 | A1 | 1/2012 | Shimuta et al. |
| 2012/0215275 | A1* | 8/2012 | Wenzel .............. A61B 5/02125 607/19 |
| 2014/0073969 | A1* | 3/2014 | Zou .................... A61B 5/02108 600/479 |
| 2014/0187990 | A1* | 7/2014 | Banet .................. A61B 5/6822 600/515 |

FOREIGN PATENT DOCUMENTS

| | | | |
|---|---|---|---|
| TW | 201023823 | A | 7/2010 |
| TW | 201424681 | A | 7/2014 |
| WO | 01-075766 | A1 | 10/2001 |
| WO | 2009138927 | A1 | 11/2009 |
| WO | 2014089665 | A1 | 6/2014 |

OTHER PUBLICATIONS

International Search Report and Written Opinion dated Jan. 12, 2016, issued in corresponding International Application No. PCT/US2015/050794, 12 pages.
Final Office Action dated Oct. 17, 2016, issued in related U.S. Appl. No. 14/563,807, filed Dec. 8, 2014.
Office Action in Primary Examination dated Dec. 28, 2016, issued in related Taiwan Patent Application No. 104136322, 19 pages.
Schwartz, Gregor, et al. "Flexible polymer transistors with high pressure sensitivity for application in electronic skin and health monitoring." Nature communications 4 (2013): 1859.
Baxi et al, "Sensing of a User's Physiological Context Using a Computing Device," Intel Corporation; U.S. Appl. No. 14/563,807, filed Dec. 8, 2014; 33 pages.
Cattivelli et al., "Noninvasive Cuffless Estimation of Blood Pressure from Pulse Arrival Time and Heart Rate with Adaptive Calibration," Body Sensor Networks 2009; 6 pages.
International Search Report and Written Opinion, dated Dec. 28, 2015, issued in corresponding International Application No. PCT/US2015/050802, 12 pages.
Non-Final Office Action dated Apr. 12, 2016, issued in related U.S. Appl. No. 14/563,807, filed Dec. 8, 2014.
Decision of Rejection in Primary Examination dated May 31, 2017, issued in related Taiwan Patent Application No. 104136322, 10 pages.
International Preliminary Report on Patentability dated Jun. 22, 2017, issued in related International Application No. PCT/US2015/050794, 5 pages.
Non-Final Office Action dated Mar. 9, 2017, issued in related U.S. Appl. No. 14/563,807, filed Dec. 8, 2014, 15 pages.
Taiwan Office Action dated Apr. 23, 2018, issued in related Appln. No. 104136322, 33 pages.

* cited by examiner

OPPORTUNISTIC MEASUREMENTS AND PROCESSING OF USER'S CONTEXT

FIELD

Embodiments of the present disclosure generally relate to the field of sensor devices, and more particularly, to providing opportunistic measurements of user's physiological context.

BACKGROUND

Today's computing devices may provide for sensing and rendering to user some user context parameters, such as user's movements, ambient light, ambient temperature, and the like. The user context parameters may be provided by adding relevant sensors and corresponding logic to a user's computing device. However, the existing methods for provision of the user's context, such as parameters related to user's state of health may consume substantial amount of user's time, and involve continuous sensor readings and corresponding data processing, which may require using substantial energy, hardware, and computing resources.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

Embodiments of the present disclosure include techniques and configurations for opportunistic measurements of user's physiological context. Opportunistic measurements may include measurements of user's context during user's interaction with an apparatus, e.g., when portions of user's upper limbs (e.g., hands, palms, and/or wrists) are disposed on the work surface of the apparatus.

In accordance with embodiments, the apparatus may comprise a sensor module that includes one or more sensors disposed on a work surface to maintain direct or indirect contact with portions of user's upper limbs, such as hands, palms, or wrists for at least a determined time period when the portions of user's upper limbs (e.g., hands, palms, or wrists) are disposed on the work surface, e.g., to interact with the apparatus, to obtain readings of first and second parameters of user's context over the determined time period of the direct or indirect contact. The apparatus may further comprise a processing module coupled with the sensor module to process the readings of the first and second parameters. Processing may include to identify at least one feature of the first parameter and one feature of the second parameter that is temporally correlated with the first feature, and determine a third parameter of the user's context based at least in part on the identified features.

The example embodiments describe contact between different portions of user's limbs, such as hands, palms, or wrists, and the sensors (e.g. electrodes) of the apparatus. Different other embodiments may be contemplated, wherein other portions of user's limbs may interact with the apparatus, allowing for measurements of the user's context, such as elbows, forearms, and the like.

In the following detailed description, reference is made to the accompanying drawings that form a part hereof, wherein like numerals designate like parts throughout, and in which are shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical, electrical, or optical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

Figure 1:
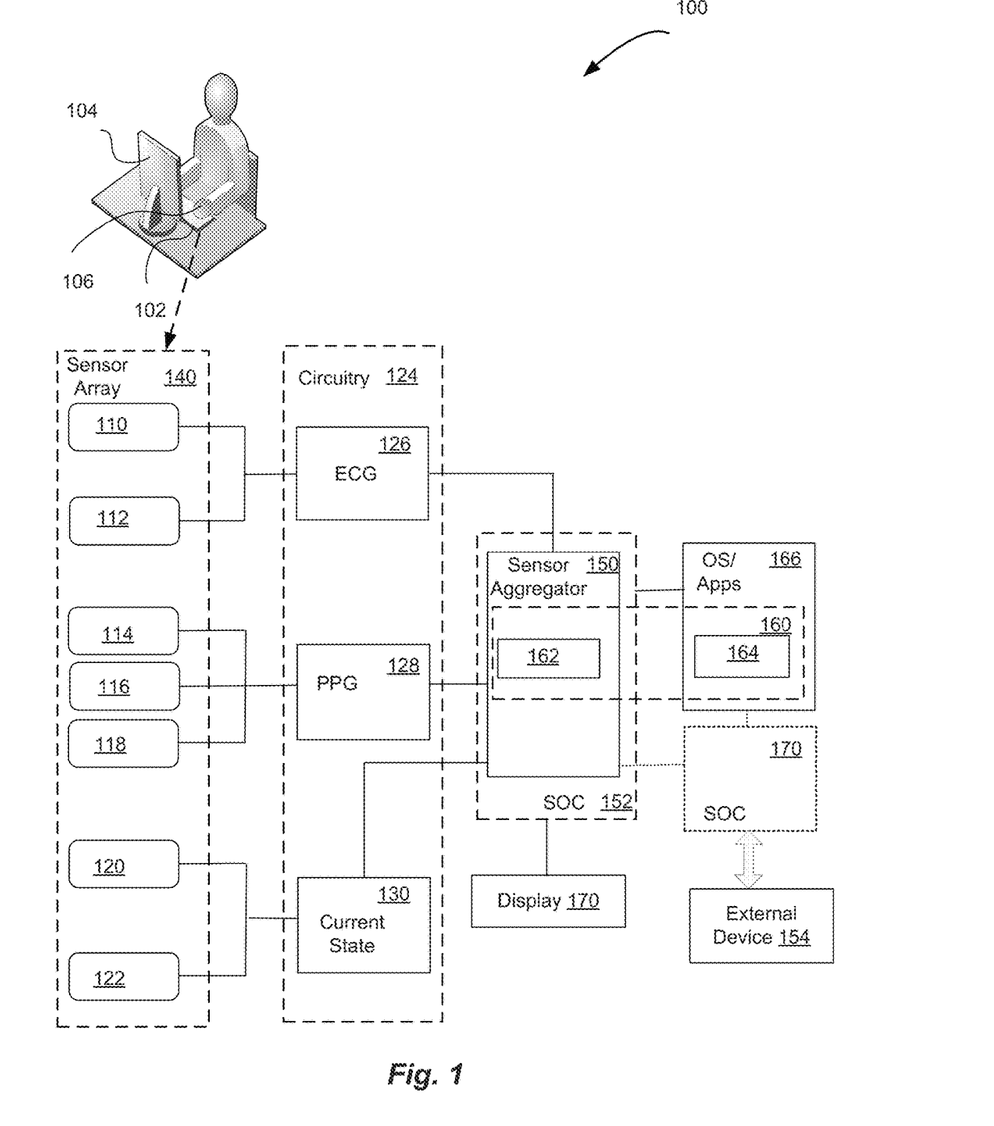
FIG. 1 is a block diagram illustrating an apparatus 100 for opportunistic measurements and processing of user's context, incorporated with the teachings of the present disclosure, in accordance with some embodiments.

FIG. 1 is a block diagram illustrating an apparatus 100 for opportunistic measurements and processing of user's context, incorporated with the teachings of the present disclosure, in accordance with some embodiments. The apparatus 100 may comprise a work surface 102, e.g., a portion of a keyboard (such as, a plane in front of the keyboard, or keyboard keys), a bezel, a back side, or other part of a computing device 104 that may be accessed by the portions of user's limbs (e.g., hands, palms or wrists) when interacting with the apparatus 100. The work surface 102 may include a sensor array 140. The sensor array 140 may include one or more sensors (e.g., electrodes) 110, 112, and other sensors 114, 116, 118, 120, 122 disposed on the work surface to directly or indirectly (e.g., when the sensors are covered by, or placed behind, an enclosure of the apparatus 100) contact with user's hands, palms, or wrists 106, when the user's hands, palms, or wrists are disposed on the work surface 102 to interact with the apparatus 100, to obtain one or more parameters of user's context (e.g., physiological context).

Different types of sensors providing readings of user's context may be disposed on (e.g., embedded in) the work surface 102 and, more generally, about the apparatus 100. The electrodes 110, 112, and sensors 114, 116, 118, 120, 122 may provide readings related to various user body functions and current physiological state. For example, at least some of the sensors 110, 112, 114, 116, 118, 120, 122 may be placed on the keyboard of a laptop or desktop computer or on the bezel or back side of a tablet computer in positions where users rest their fingers and palms or wrists naturally. For example, electrodes 110, 112 may be configured to measure electrocardiogram (ECG) bio-potentials from the user's hands, palms, or wrists 106. Electrodes 110, 112, may form an electrically conductive pattern on the work surface 102, for example.

Sensors 114, 116, 118 may comprise optical sensors to provide photoplethysmographic (PPG) measurements. The optical sensors 114, 116, 118 may comprise a combination of photodetectors and light-emitting diodes (LED) configured to detect a flow of blood, e.g., to user's fingers or palms placed around the work surface 102, from which data blood pressure of the user may be derived (e.g., in combination with ECG readings). Sensors 120, 122 may comprise other types of sensors configured to measure current physiological state of the user. More specifically, sensors 120, 122 may measure motions of the user in relation to the apparatus 100 (e.g. computing device 104), jitter associated with user interaction with the computing device 104 (e.g., user's interaction with a keyboard, touchscreen, or touchpad of the computing device 104), user's body skin temperature, and the like. For example, sensors 120, 122 may include one of accelerometer, gyroscope, temperature sensor, or the like.

Before further describing the elements of FIG. 1, it should be noted that the number of electrodes and sensors illustrated and types of sensors provided are for illustration purposes only and are not to be construed as limiting on this disclosure.

The apparatus 100 may further comprise electronic circuitry 124 coupled with the sensor array 140, to collect parameters of the user's context while the direct contact between user's hands, palms, or wrists and work surface including at least some of the sensors is maintained, thus enabling opportunistic measurements of the user's context. The circuitry 124 may include ECG module 126 to receive and pre-process readings of ECG measurements provided by sensors 110, 112, and PPG module 128 to receive and pre-process readings of PPG measurements provided by sensors 114, 116, 118. The circuitry 124 may further include current state sensor module 130 to receive and pre-process readings associated with the current state of user and provided by sensors 120, 122. The circuitry 124 may include, for example, an amplifier, an analog-to-digital converter (ADC) and a controller to operate the circuitry 124. In some embodiments, the circuitry 124 may be integrated in a form of an integrated circuit (IC).

The apparatus 100 may further include a sensor aggregator (e.g., sensor hub) 150 coupled with circuitry 124 and configured to aggregate data pre-processed by circuitry 124 and further process the data. In some embodiments, the sensor aggregator 150 may be integrated on a system on chip (SOC) 152, as indicated by the dashed contour line. In some embodiments, the sensor aggregator 150 may be coupled with operating system and/or applications (OS/Apps) 166, which in some embodiments may be integrated on SOC 152, as indicated by the dotted contour line. The sensor aggregator 150 may comprise a common low-power sensor hub, to allow opportunistic sensing whenever the user maintains direct (or indirect) contact between her hands (palms, wrists) 106 and the sensors of the sensor array 140.

The apparatus 100 may further include a processing module 160 configured to process the readings provided by the sensors circuitry 124. The processing module 160 may include a blood pressure determination sub-module 162 disposed with sensor aggregator 150 and configured to process the readings of the first and second parameters (e.g., ECG and PPG), identify at least one feature of the first parameter and another feature of the second parameter that is temporally correlated with the feature of the first parameter, and determine a third parameter, e.g. blood pressure (BP) of the user's context based at least in part on the identified first and second features.

The processing module 160 may further include a blood pressure boundary determination sub-module 164 disposed with OS/Apps 166, and configured to, based on the jitter data, motion data, systolic blood pressure (SBP) data, and diastolic blood pressure (DBP) data, to determine boundary values of the third parameter (e.g., BP) for the user, based at least in part on the user's physiological state indicated by the jitter data and motion data. The provision of BP and its boundaries may be done empirically or heuristically, e.g., using machine-learning algorithms described below in greater detail.

In some embodiments, the processing module 160 may be distributed among the components of the apparatus 100 in other manners. For example, the sub-modules 162 and 164 may reside on the sensor aggregator 150 and may execute on the sensor aggregator 150's processor. In some embodiments, the sub-modules 162 and 164 may reside with the OS/App 166 and may execute on a central processing unit (CPU) (not shown) of the apparatus 100.

The apparatus 100, in addition to the illustrated elements and the mentioned CPU, may include other components necessary for the functioning of the apparatus 100. For example, the processing unit 160 may be coupled with one or more interfaces (not shown) to communicate the user's context measurements over one or more wired or wireless network(s) and/or with any other suitable device, such as external computing device 154. The apparatus may further include a display 170 to display results of opportunistic measurements and processing of the user's context.

Depending on a type of the apparatus 100, different components of the apparatus may physically reside in different portions of the apparatus. For example, if the apparatus 100 comprises a tablet computer or smart phone, components 140, 124, 150, and 166 may reside in the body of the tablet or smart phone. If the apparatus 100 comprises a laptop or desktop computer, components 140, 124, and 150 may reside inside a keyboard, and the component 166 may reside inside the memory of the computer, which may be communicatively coupled with the other components via interconnect such as universal serial bus (USB) or serial peripheral interface (SPI).

The data from ECG sensors 110, 112, and PPG sensors 114, 116, 118 may be captured opportunistically, for example as user puts the palms (or wrists) on ECG sensors 112, 114 and fingertips on the keys with PPG sensors 114, 116, 118. To ensure meaningful sensor readings, the sensor data may be captured over a determined period of time, for example, at least for five seconds. Optimum time for capturing sensor readings may be empirically configured for the apparatus 100. The captured sensor data may be time stamped as it is captured from the sensors.

The data from ECG sensors and from PPG sensors may be captured in a correlated fashion, to ensure meaningful results of processing the captured sensor data. As described above, sensors 114, 116, 118 may comprise a combination of photodetectors and light source (e.g., LED) configured to detect a flow of blood, e.g., to user's fingers or palms placed around the work surface 102. Accordingly, light from the light source may be used to indirectly measure heart beat rate and peripheral capillary oxygen saturation (SpO2) by measuring the volume of blood vessels under the skin, to provide PPG readings. Two or more electrodes (e.g., 110, 112), placed in specific areas of the apparatus 100, may be used to directly measure the hearts electrical activity and heartbeat rate of the user, to provide ECG readings. Electrodes 110, 112 may be placed such as to be positioned on opposite sides, and distant from, the user's heart. Electrodes 110 and 112 may be used to sense ECG bio-potentials from left and right hands, palms, or wrists 106 of the user.

To allow for opportunistic sensing, sensors of the sensor array 140 may be accessible to the user in natural positions and activities. There may be several options for placement of these sensors on devices. As described above, apparatus 100 may include a work surface 102, for example, a surface of the computing device 104, such as computing device keyboard, which may come in direct contact with user's hands, palms, or wrists 106 when the user operates the keyboard. In another example, a computing device may comprise a tablet or smartphone, and work surfaces may comprise bezels or back sides of the devices. Some of the examples of sensor placement on work surfaces of various computing devices are described below.

Figure 2:
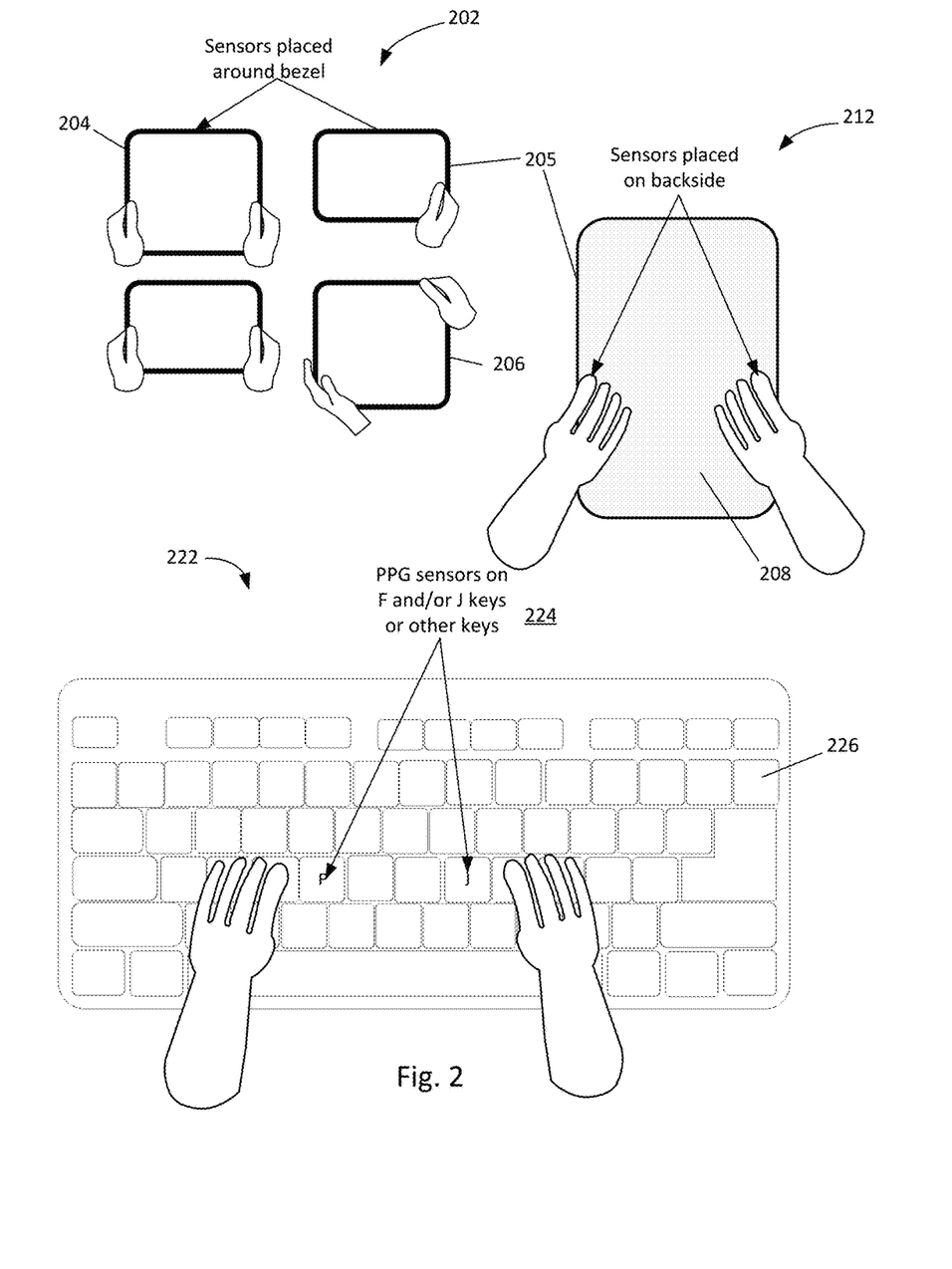
FIG. 2 illustrates examples of disposition of sensors on work surfaces of computing devices, to enable measurements of user's context, in accordance with some embodiments.

It should be noted that the apparatus 100 may take a number of different forms, in addition or in the alternative to described herein. For example, apparatus 100 may take on many different forms, e.g., headsets, glasses, wands or styluses that contain compute components, and the like. Accordingly, different body parts (e.g., forehead, eyes, ears, etc.), in addition or in the alternative to limb portions, such as hands, palms or wrists, may be in direct or indirect contact with different forms of work surfaces of computing devices of different types, to enable user's context measurements and processing described herein. FIG. 2 illustrates examples of disposition of sensors on work surfaces of computing devices, to enable measurements of user's context, in accordance with some embodiments. View 202 illustrates the placement of the sensors around a bezel 204 of a casing 205 of a tablet computing device 206. View 212 illustrates the placement of the sensors around a back side 208 of the casing 205 of a tablet computing device (e.g., 206) or smart phone. View 222 illustrates the placement of the sensors on a keyboard 226 of a computing device, such as a laptop, tablet (if equipped with a keyboard), or desktop computer. As shown, the sensors may be disposed on particular keys 224 of the keyboard 226.

Accordingly, a casing with a work surface suitable for placing the sensors for measurements of a user's context may include at least a portion of a keyboard of a computing device, a bezel of the computing device, or a back side of the computing device. In summary, a computing device, on which the sensors for opportunistic measurements of the user context may be placed, may include a laptop computer, a desktop computer, a tablet computer, a smart phone, or any other mobile or stationary computing device.

Figure 3:
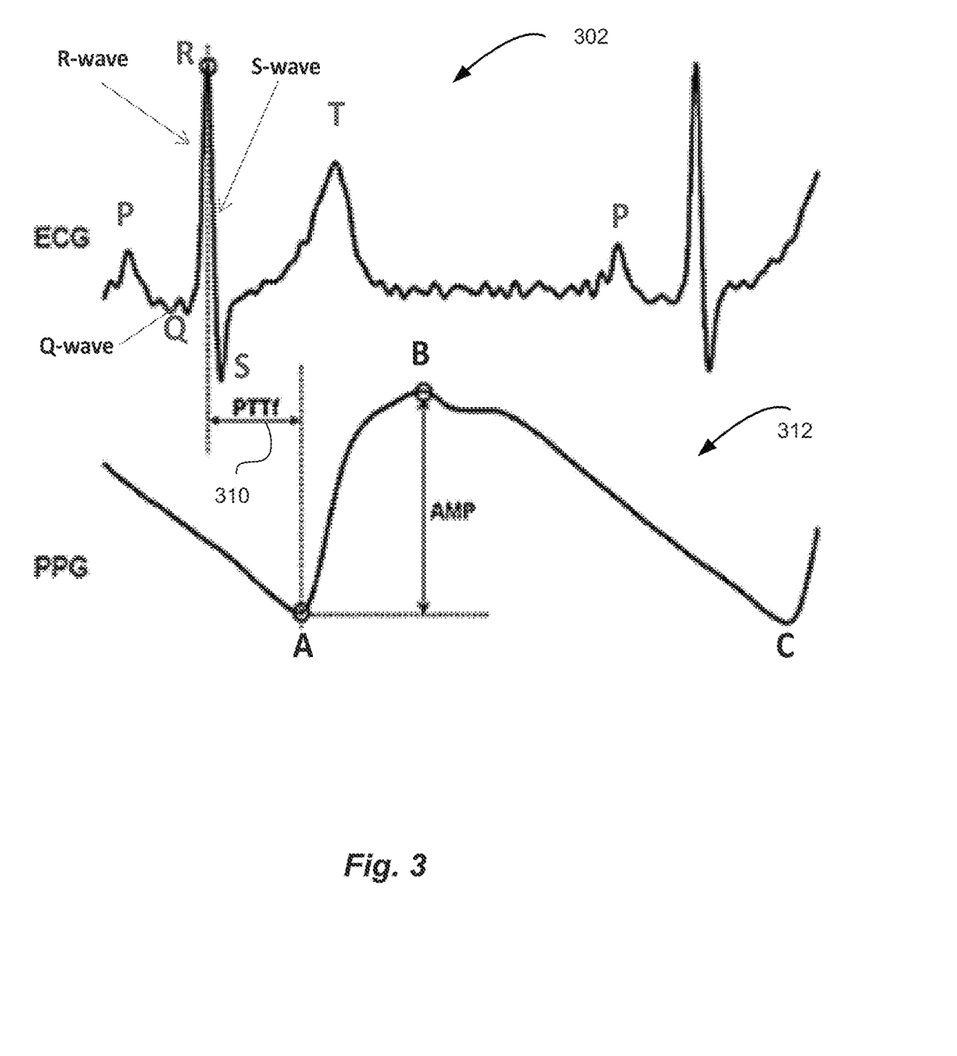
FIG. 3 is a graphical representation illustrating a time-correlated view of an example graphs representing sensor data received in response to opportunistic measurements of user's context, to be processed in accordance with some embodiments.

FIG. 3 is a graphical representation illustrating a time-correlated view of an example ECG graph 302 and PPG graph 312, representing sensor data received in response to opportunistic measurements of user's context, to be processed in accordance with some embodiments. For example the user may put the palms or wrists on ECG sensors on the keyboard 226 and fingertips on the keys 224 with PPG sensors, as shown in view 222 of FIG. 2. As described above, the ECG and PPG data may be captured for a determined period of time, such as at least for 5 seconds. The ECG and PPG data represented by graphs 302 and 312 may be time-stamped as it is captured from the sensors. As shown by graphs 302 and 312, the ECG and PPG data may represent the signal amplitude ECG and PPG data in time domain. As described below, some features (points of interest) shown in graphs 302 and 312 may have temporal correlation. Further, at least some features of graph 302 (ECG parameter), temporally correlated with features of graph 312 (PPG parameter), may provide correlation with another parameter of user's context (e.g., blood pressure) that may be empirically derived from the temporal correlation of the ECG and PPG features.

As shown in graph 302, the points of interest, such as peaks and slopes of the QRS complex of the ECG graph are marked by points Q, R, and S. As shown, the QRS complex may include three waves. Q-wave may indicate the downward deflection of the ECG signal. R-wave may indicate the upward deflection from point Q to point R. S-wave may indicate the downward deflection from point R to point S. Other points of interest in graph 302 may include a P-wave before the QRS complex and a T-wave following the QRS complex.

As shown in graph 312, the points of interest in the PPG data may include point A (foot), which marks a start of the user's pulse detected by PPG sensors, and point B (peak), which marks the end of the detected pulse. It is to be noted that point C shown in graph 312 is the point A of the next pulse cycle.

A first feature (point of interest) of graph 302 may comprise an R peak of a QRS complex of the ECG data. The second feature of graph 312 may comprise a lowest point A in the PPG curve of the PPG data. The temporal correlation between the first and second features comprises a pulse transit time (PTT) 310, wherein the PTT 310 is a period of time that elapses between the R peak of the QRS complex of the ECG data and the lowest point A in the PPG curve. Accordingly, PTT 310 may indicate a time period that takes the pulse pressure wave to propagate through a length of the arterial tree of the user's body before it arrives to an end point (e.g., user's finger) and may be detected by PPG sensors as described above.

Put simply, PTT 310 may indicate the time period from a peak in heart rate to a time instance when blood pumped by the heart at a peak rate arrives in body's fingers, reflected in graph 312 as point A that indicates a beginning of the user's heart's pulse. Accordingly, one skilled in the art will appreciate that there may be a correlation of points R (graph 302) and A (graph 312), or PTT 310, with blood pressure. This correlation, when determined (e.g., empirically or heuristically), may provide an estimation of the blood pressure parameter based on the PTT 310. Furthermore additional features may be extracted from graphs 302 and 312 may be used to contribute to empirical estimation of blood pressure as described below.

The additional features (points of interest) may include a set of values associated with the QRS complex of graph 302 and another of values associated with an amplitude characteristic of the PPG curve and upward and downward slope characteristics of the PPG curve in graph 312. More specifically, the features to be extracted from graphs 302 and 312 may include the following:

$x_1$: PR interval—measured from the beginning of P-Wave to the peak of QRS complex;

$x_2$: QRS duration—measured from the start of the Q-wave to end of the S-wave;

$x_3$: QT interval—measured from the start of QRS complex to end of T-wave;

$x_4$: Q-wave slope—downward slope just before point Q;

$x_5$: R-wave slope—upward slope from point Q to point R;

$x_6$: S-wave slope—downward slope from point R to point S;

$x_7$: PTT (312)—time elapse between point R on ECG curve (graph 302) to point A on the time-correlated PPG curve (graph 312), as described above;

$x_8$: P-slope—Maximum slope between A and B points of the PPG curve;

$x_9$: P-Amp—Amplitude of the PPG peak;

$x_{10}$: P-decline—downward slope between point B and point C of the PPG curve;

$x_{11}$: Heart-Rate—Average frequency of point R of the QRS curve.

The above values may be averaged over a determined period of time that the readings may take, such as five second time window as described above. Based on the above features, an empirical correlation between the features and a parameter to be derived from the correlation (e.g., blood pressure) may be derived. For example, a machine-learning algorithm (e.g., linear regression algorithm) may be applied to the above features to establish empirical correlation between the features and derive the blood pressure parameter from the correlation. More specifically, linear regression equations for systolic blood pressure (SBP) and diastolic blood pressure (DBP) in terms of the extracted features may be created and coefficients minimizing a cost function may be determined For example, a generic equation in a linear regression model is of the form $$h_\theta(x) = \theta_0 + \theta_1 x_1 + \theta_2 x_2 + \ldots + \theta_n x_n \quad (1)$$

where $x_n$ is one of the feature in the feature set. This may be rewritten in a matrix representation:

$$h_\theta(x) = \theta^T X \quad (2)$$

where X is the feature matrix, and Q is the co-efficient matrix.

The machine-learning algorithm may be applied to find the coefficients that minimize the cost function, which is the difference in magnitude of the values of hθ(x) and the values from training set (e.g., ground truth values). The cost function may be defined as $$J(\theta) = \frac{1}{2m} \sum_{i=1}^{m} (h_\theta(x^{(i)}) - y^{(i)})^2 \quad (3)$$

where y is the ground truth.

The goal of the machine-learning algorithm is to minimize the cost function. Different methods to minimize the cost function and solve the linear regression problem are known to people skilled in the art and are not the subject of this disclosure.

Accordingly, equations covering SBP and DBP may be created based on above considerations. More specifically, the equation covering SPB may be provided:

$$SBP(x) = \theta_0 + \theta_1 x_1 + \theta_2 x_2 + \ldots + \theta_n x_n \quad (4)$$

where $x_i$ is a numerical feature value extracted/computed from as described above. The equation (4) may be rewritten according to (2):

$$SBP(X) = \theta^T X \quad (5)$$

Similarly, the equation covering DPB may be provided:

$$DBP = \psi_0 + \psi_1 x_1 + \psi_2 x_2 + \ldots + \psi_n x_n \quad (6)$$

The equation (4) may be rewritten according to (2):

$$DBP(X) = \psi^T X \quad (7)$$

The training data may contain the ground truth that may be obtained, for example, using traditional blood pressure measurement method. The traditional method may be used just once to collect the training data. The model may be developed using the training data, and the two sets of coefficients matrices θ and ψ (one for SBP and one for DBP) may be calculated.

Using the apparatus described in reference to FIG. 1, the parameters related to user's physiological context (e.g., ECG and PPG) may be measured, the features defined above may be determined, the coefficients and feature values may be applied to the equations, and the blood pressure parameter may be calculated and reported to the user. It will be appreciated that the described technique may not require training for each user and may be applied for multiple different users. Further refinements may be done to the coefficients matrix Q if the user may desire to further train the model.

The ECG and PPG parameters, and blood pressure derived from ECG and PPG may characterize user's physiological context. As described in reference to FIG. 1, sensors of the sensor array 140 may be used to provide readings indicating different aspects of the user's physiological context, such user's current physiological state. For example, jitter data associated with the direct contact between the user's hands, palms, or wrists and the work surface, motion data associated with the direct contact between the user's hands, palms, or wrists and the work surface may be collected using the apparatus 100 of FIG. 1. The features that may be used to describe user's current physiological state may include:

y1: Touchscreen Jitter (e.g., % value);

y2: Touchpad jitter (e.g., % value);

y3: Keyboard Jitter (e.g., % value);

y4: 3-axis Accelerometer value (e.g. g-compensated, magnitude);

y5: Motion data (e.g., data reflecting stationary and in-motion states of the user).

A machine-learning algorithm may be applied to the jitter data, motion data, SBP data, and DBP data, to determine boundary values of the blood pressure for the user, based at least in part on the user's current physiological state. The machine-learning algorithm may comprise a logistic regression model, for example.

Based on the jitter and motion data, SBP and DBP may be classified into different categories, for example, blood pressure normal, blood pressure lower than normal limits, and blood pressure higher than normal limits. The boundary values for the normal blood pressure range for a user may be determined, the deviations from the normal state may be learned, and the model may be adapted (e.g., boundary values may be adjusted) accordingly.

User's physiological state may be determined (e.g., through readings of relevant sensors) and correlated with the blood pressure data. The logistic regression model may be self-trainable. The normal boundary (threshold) blood pressure values may be adjusted as the user is interacting with the input components of a computing device (e.g., keyboard, touch screen, etc.). Jitter data below a certain threshold may constitute stable physiological condition of the user and serve as ground truth data to adjust the normal blood pressure value boundaries over time.

The model may be initially trained (e.g., by user) by providing occasional feedback (ground truth) for a period of time (e.g., several days). A mechanism to collect the data may be implemented, for example, by periodic display (e.g., about 4-5 times in a day) of a dialog box asking the user if he or she is feeling normal (e.g., as usual). The system may capture the user response as the ground truth data, and record the data with the average values of measurements $y_1$ through $y_5$ over a determined period of time, for example, prior to displaying the dialog box and subsequent to displaying the dialog box (e.g. five minutes prior to displaying the dialog box and five minutes after displaying the dialog box).

Once the data is collected for a period of time (e.g., three to five days), the system may create a logistic regression model. As known, a logistic regression model may be similar to the linear regression model with the output being a fraction value between 0 and 1. This may be obtained by the equation below:

$$h_\theta(y) = g(\varphi^T Y)$$

where g is a sigmoid function, i.e. $g(z)=1/(1+e^{-z})$, returning a value between 0 and 1 for all values of z.

Y is the input matrix from the features $y_1$ through $y_5$ from the data. $\varphi$ is the coefficient matrix created by running the logistic regression model (similar to what was described earlier with linear regression model) during the training of the model.

For example, a value of 0.7 returned by the model may indicate that there is a probability of 70% that the user is in "normal" state. A value of 0.3 may indicate that such probability is 30%. A threshold value may be determined to indicate a "normal" state of the user. For example, a threshold value of 80% (i.e. value 0.8 and above) may be used to determine that the user is in "normal" state of health.

During runtime, the measurements y1 through y5 may be made along with ECG and PPG data collection, using sensors 120, 122, for example. A determination of the user's current state may be done using the Y values and the $\varphi$ matrix from the trained model. Thus, at the end of each runtime cycle, the model output may include a DBP value, an SBP value, and a boolean value indicating whether the user is currently in "normal" state of health.

The system may maintain average (nominal) values of DBP and SBP (DBPavg and SBPavg). If the user state is determined to be "normal," then the current recorded value of DBP and SBP may be used to adjust the values:

$$DBPavg = ((DBPavg*n)+DBP)/(n+1) \quad (9)$$

where n is the running count of number of readings taken, and is incremented every time this calculation is made. Similarly, $$SBPavg = ((SBPavg*n)+SBP)/(n+1) \quad (10)$$

If the user state was determined to be not normal, the values may not be used to update the normal values, and may be ignored from the calculation.

At the end of every calculation cycle, the system may have four determined values, DBP, DBPavg, SBP, and SBPavg. These values may be used to notify the user about his or her current state based on the following logic:
If (DBP>(DBPavg+10) and SBP>(SBPavg+10)), then notify user that his or her blood pressure is higher than usual;
If (DBP<(DBPavg−10) and SBP<(SBPavg−10)), then notify user that his or her blood pressure is lower than usual.

If only one value (DBP or SBP) is outside the range (+/−10) then the user may be prompted by a notification calling his or her attention to his or her current state. For example, a dialog box may be displayed with a question: "Are you feeling OK? Yes/No" and the user's response may be used to further train the logistic regression model as part of the continuous learning model.

Figure 4:
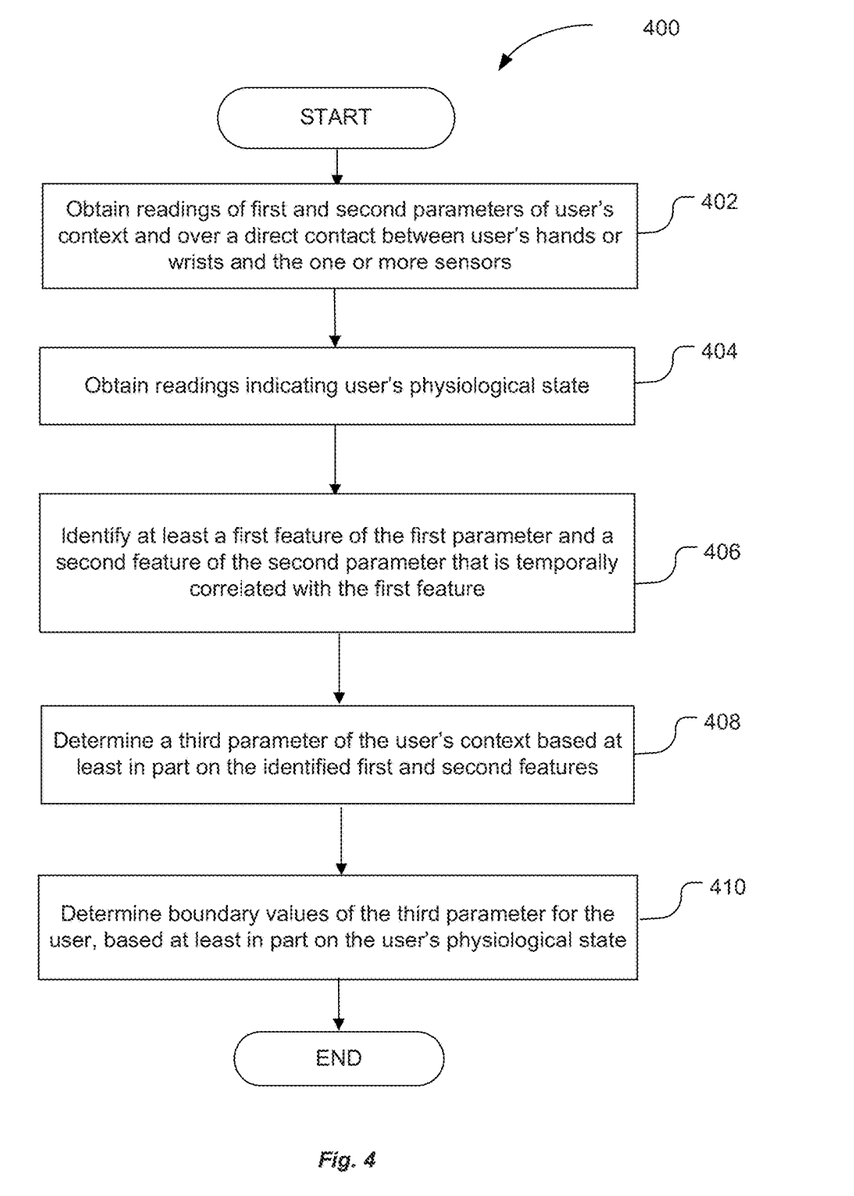
FIG. 4 is a process flow diagram for opportunistic measurements and processing of user's context, in accordance with some embodiments.

FIG. 4 is a process flow diagram for opportunistic measurements and processing of user's context, in accordance with some embodiments. The process 400 may comport with and be performed by some of the elements of the various embodiments earlier described in reference to FIGS. 1-3. In alternate embodiments, the process 400 may be practiced with more or less operations, or different order of the operations.

The process 400 may begin at block 402 and include obtaining, from one or more sensors, e.g., sensors disposed on a work surface of the computing device, readings of first and second parameters of user's context over a determined time period of a direct contact between user's hands, palms, or wrists and the one or more sensors. The user's context may comprise user's physiological context and user's physiological state, wherein the first, second, and third parameters may relate to the user's physiological context. For example, the first, second, and third parameters may comprise ECG, PPG, and BP respectively.

At block 404, the process 400 may further include obtaining, readings indicating the user's physiological state, during the maintenance of the direct contact between the user's hands, palms, or wrists and the one or more sensors disposed on the work surface.

At block 406, the process 400 may include identifying, from the obtained readings of the first and second parameters, at least a first feature of the first parameter and a second feature of the second parameter that is temporally correlated with the first feature. The process 400 may further include identifying, at block 404, a first plurality of features of the first parameter and a second plurality of features of the second parameter, wherein the first plurality of features includes the first feature and the second plurality of features includes the second feature, and determining empirical correlation between the first and second pluralities of features.

At block 408, the process 400 may include determining a third parameter of the user's context based at least in part on the identified first and second features. The third parameter may be further determined based on the empirical correlation between the first and second pluralities of features determined at block 404.

At block 410, the process 400 may include determining the boundary values of the third parameter for the user, based at least in part on the user's physiological state.

Figure 5:
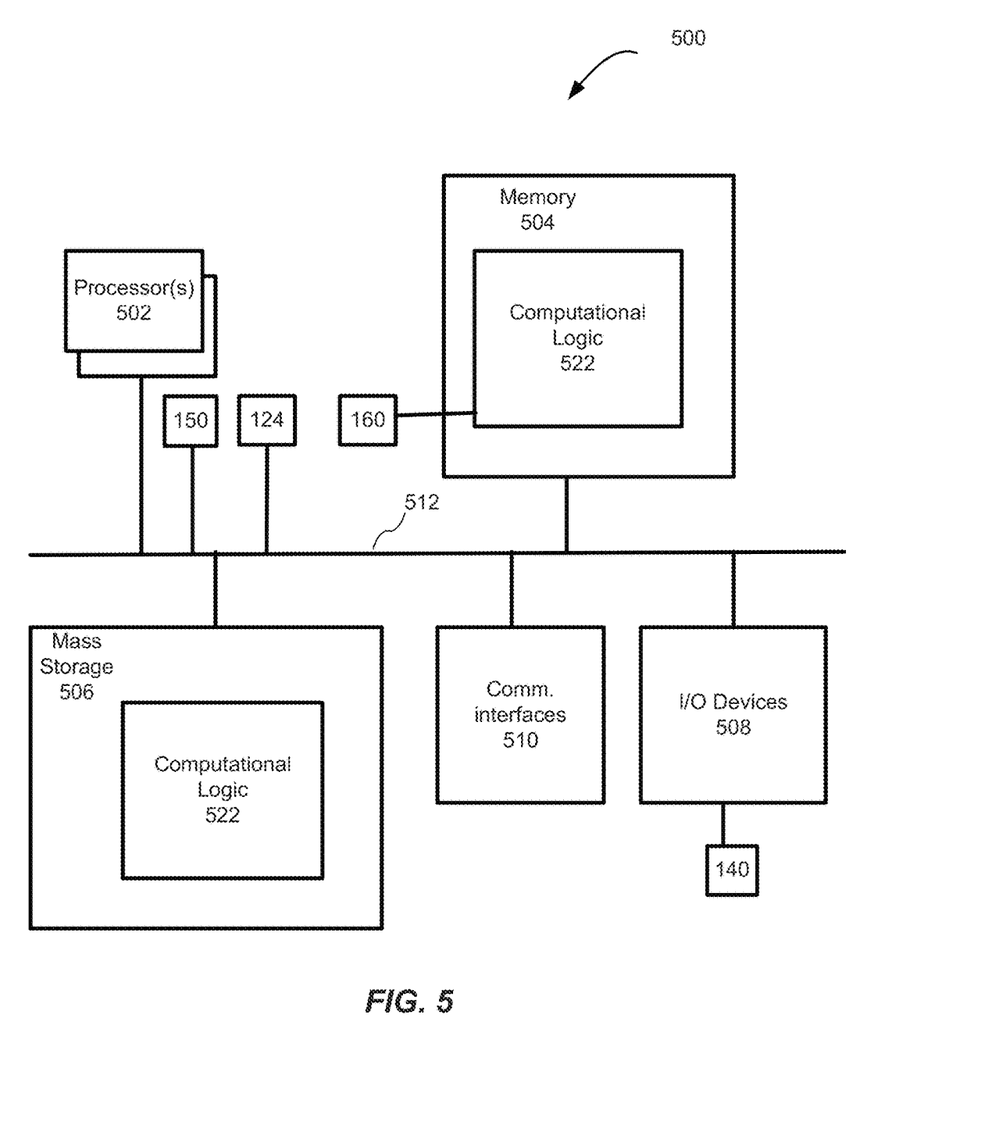
FIG. 5 illustrates an example computing device suitable for use with various components of FIG. 1, such as apparatus for opportunistic measurements and processing of user's context of FIG. 1, in accordance with some embodiments.

FIG. 5 illustrates an example computing device 500 suitable for use with various components of FIG. 1, such as apparatus 100 for opportunistic measurements and processing of user's context of FIG. 1, in accordance with some embodiments. In some embodiments, example computing device 400 may include various components of apparatus 100, e.g., the circuitry 124, sensor array 140, sensor aggregator 150, and processing module 160 described in reference to FIG. 1.

As shown, computing device 500 may include one or more processors or processor cores 502 and system memory 504. For the purpose of this application, including the claims, the terms "processor" and "processor cores" may be considered synonymous, unless the context clearly requires otherwise. The processor 502 may include any type of processors, such as a central processing unit (CPU), a microprocessor, and the like. The processor 502 may be implemented as an integrated circuit having multi-cores, e.g., a multi-core microprocessor. The computing device 500 may include mass storage devices 506 (such as solid state drives, volatile memory (e.g., dynamic random-access memory (DRAM), and so forth). In general, system memory 504 and/or mass storage devices 506 may be temporal and/or persistent storage of any type, including, but not limited to, volatile and non-volatile memory, optical, magnetic, and/or solid state mass storage, and so forth. Volatile memory may include, but is not limited to, static and/or dynamic random-access memory. Non-volatile memory may include, but is not limited to, electrically erasable programmable read-only memory, phase change memory, resistive memory, and so forth.

The computing device 500 may further include input/output (I/O) devices 508 (such as a display (e.g., display 170 of FIG. 1), soft keyboard, touch sensitive screen, image capture device, and so forth) and communication interfaces 510 (such as network interface cards, modems, infrared receivers, radio receivers (e.g., Near Field Communication (NFC), Bluetooth, WiFi, 4G/5G LTE), and so forth).

The communication interfaces 510 may include communication chips (not shown) that may be configured to operate the device 500 in accordance with a Global System for Mobile Communication (GSM), General Packet Radio Service (GPRS), Universal Mobile Telecommunications System (UMTS), High Speed Packet Access (HSPA), Evolved HSPA (E-HSPA), or Long-Term Evolution (LTE) network. The communication chips may also be configured to operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). The communication chips may be configured to operate in accordance with Code Division Multiple Access (CDMA), Time Division Multiple Access (TDMA), Digital Enhanced Cordless Telecommunications (DECT), Evolution-Data Optimized (EV-DO), derivatives thereof, as well as any other wireless protocols that are designated as 3G, 4G, 5G, and beyond. The communication interfaces 510 may operate in accordance with other wireless protocols in other embodiments.

The above-described computing device 500 elements may be coupled to each other via system bus 512, which may represent one or more buses. In the case of multiple buses, they may be bridged by one or more bus bridges (not shown). Each of these elements may perform its conventional functions known in the art. In particular, system memory 504 and mass storage devices 506 may be employed to store a working copy and a permanent copy of the programming instructions implementing the operations associated with the apparatus 100, such as sub-modules 162 and 164 described in reference to the processing unit 160 of FIG. 1. The various elements may be implemented by assembler instructions supported by processor(s) 502 or high-level languages that may be compiled into such instructions.

The permanent copy of the programming instructions may be placed into permanent storage devices 506 in the factory, or in the field, through, for example, a distribution medium (not shown), such as a compact disc (CD), or through communication interface 510 (from a distribution server (not shown)). That is, one or more distribution media having an implementation of the agent program may be employed to distribute the agent and to program various computing devices.

The number, capability, and/or capacity of the elements 508, 510, 512 may vary, depending on whether computing device 500 is used as a stationary computing device, such as a set-top box or desktop computer, or a mobile computing device, such as a tablet computing device, laptop computer, game console, or smartphone. Their constitutions are otherwise known, and accordingly will not be further described.

At least one of processors 502 may be packaged together with computational logic 522 configured to practice aspects of embodiments described in reference to FIGS. 1-4. For one embodiment, at least one of processors 502 may be packaged together with memory having computational logic 522 to form a System in Package (SiP) or a System on Chip (SoC). For at least one embodiment, the SoC may be utilized in, e.g., but not limited to, a computing device such as a laptop, desktop, computing tablet or smartphone.

In embodiments, the computing device 500 may include at least some of the components of the apparatus 100 as described above. In some embodiments, the apparatus 100 may include sensor array 140 (e.g., disposed on a keyboard of the computing device 400). Circuitry 124, sensor aggregator 150, and processing module 160 and may be communicatively coupled with various elements of the computing device 500 as shown in FIG. 5 and described herein.

In various implementations, the computing device 500 may comprise a laptop, a netbook, a notebook, an ultrabook, a smartphone, a tablet, a personal digital assistant (PDA), an ultra mobile PC, a mobile phone, a laptop, a desktop, or any other mobile computing device. In further implementations, the computing device 500 may be any other electronic device that processes data.

The embodiments described herein may be further illustrated by the following examples.

Example 1 is apparatus for opportunistic measurements and processing of user's context, comprising: a sensor module that includes one or more sensors disposed on a work surface of the apparatus to maintain direct or indirect contact with at least portions of a user's limbs for at least a determined time period when the portions of user's limbs are disposed on the work surface, to obtain readings of first and second parameters of user's context over the determined time period of the direct or indirect contact; and a processing module coupled with the sensor module to process the readings of the first and second parameters, wherein to process includes to identify at least a first feature of the first parameter and a second feature of the second parameter that is temporally correlated with the first feature, and determine a third parameter of the user's context based at least in part on the identified first and second features Example 2 may include the subject matter of Example 1, wherein the processing module is to determine temporal correlation between the first and second features.

Example 3 may include the subject matter of Example 1, wherein the processing module to process the readings of the first and second parameters further includes to identify a first plurality of features of the first parameter and a second plurality of features of the second parameter, wherein the first plurality of features includes the first feature and the second plurality of features includes the second feature.

Example 4 may include the subject matter of Example 3, wherein the processing module to determine a third parameter of the user's context includes to apply a first machine-learning algorithm to the first and second pluralities of features to determine empirical correlation between the first and second pluralities of features, wherein the derivation of the third parameter is based at least in part on the empirical correlation between the first and second pluralities of features.

Example 5 may include the subject matter of Example 4, wherein the first machine-learning algorithm comprises a linear regression algorithm.

Example 6 may include the subject matter of Example 5, wherein the user's context comprises user's physiological context, wherein the first parameter comprises electrocardiographic (ECG) data, the second parameter comprises photoplethysmographic (PPG) data, and the third parameter comprises blood pressure (BP) data.

Example 7 may include the subject matter of Example 6, wherein the first feature comprises an R peak of a QRS complex of the ECG data, the second feature comprises a lowest point in a PPG curve of the PPG data, and the temporal correlation between the first and second features comprises a pulse transit time (PTT), wherein the PTT is a period of time that elapses between the R peak of the QRS complex of the ECG data and the lowest point in the PPG curve.

Example 8 may include the subject matter of Example 7, wherein the first plurality of features includes a first set of values associated with the QRS complex and the second plurality of features includes a second set of values associated with an amplitude characteristic of the PPG curve and upward and downward slope characteristics of the PPG curve.

Example 9 may include the subject matter of Example 6, wherein the BP data further comprises systolic blood pressure (SBP) data and diastolic blood pressure (DBP) data, wherein the processing module is to derive SBP data and DBP data from the application of the first machine-learning algorithm to the first and second pluralities of features.

Example 10 may include the subject matter of Example 9, wherein the user's context further comprises user's physiological state, wherein the sensor module is further to obtain information indicating the user's physiological state, wherein the information includes jitter data associated with the direct or indirect contact between the portions of user's limbs and the work surface, and motion data associated with the direct or indirect contact between the portions of user's limbs and the work surface.

Example 11 may include the subject matter of Example 10, wherein the processing module is further to apply a second machine-learning algorithm to the jitter data, motion data, SBP data, and DBP data, to determine boundary values of the third parameter for the user, based at least in part on the user's physiological state.

Example 12 may include the subject matter of Example 11, wherein the one or more sensors comprise at least a selected one of: a gyroscope or accelerometer.

Example 13 may include the subject matter of Example 12, wherein the one or more sensors comprise at least two or more electrodes to provide readings of the ECG data and at least one light sensor to provide readings of the PPG data.

Example 14 may include the subject matter of any of Examples 1 to 13, wherein the work surface comprises at least a selected one of: a keyboard of the apparatus, a bezel of the apparatus, or a back side of the apparatus, wherein the apparatus is a computing device, wherein the portions of user's limbs include at least one of: wrists, palms, or hands that are disposed on the work surface to interact with the apparatus.

Example 15 is an apparatus for opportunistic measurements and processing of user's context, comprising: a casing, having at least one work surface that includes one or more sensors disposed on the work surface to maintain direct or indirect contact with portions of user's limbs for at least a determined time period when the portions of user's limbs are disposed on the work surface, to obtain readings of first and second parameters of user's context over the determined time period of the direct or indirect contact; and a processing module coupled with the one or more sensors to process the readings of the first and second parameters, wherein to process includes to identify at least a first feature of the first parameter and a second feature of the second parameter that is temporally correlated with the first feature, and determine a third parameter of the user's context based at least in part on the identified first and second features.

Example 16 may include the subject matter of Example 15, wherein the processing module to process the readings of the first and second parameters further includes to: identify a first plurality of features of the first parameter and a second plurality of features of the second parameter, wherein the first plurality of features includes the first feature and the second plurality of features includes the second feature; determine empirical correlation between the first and second pluralities of features; and derive the third parameter based at least in part on the empirical correlation between the first and second pluralities of features.

Example 17 may include the subject matter of Example 16, wherein the user's context comprises user's physiological context and user's physiological state, wherein the first, second, and third parameters are related to the user's physiological state, wherein the one or more sensors is further to obtain readings indicating the user's physiological state during the maintenance of the direct or indirect contact between the portions of user's limbs and the work surface, and wherein the processing module is further to determine boundary values of the third parameter for the user, based at least in part on the user's physiological state, wherein the portions of limbs are disposed on the work surface to interact with the apparatus.

Example 18 may include the subject matter of Example 17, further comprising a sensor aggregator module coupled with the one or more sensors, to power on the one or more sensors and to pre-process the readings provided by the one or more sensors.

Example 19 may include the subject matter of Example 18, wherein the sensor aggregator module and the processing module are integrated on a system on chip (SOC), wherein the casing comprises at least a portion of a keyboard of the apparatus, a bezel of the apparatus, or a back side of the apparatus, wherein the apparatus comprises one of: a laptop computer, a desktop computer, a tablet computer, or a smart phone.

Example 20 is a computer-implemented method for opportunistic measurements and processing of user's context, comprising: obtaining, by a computing device, from one or more sensors disposed on a work surface of the computing device, readings of first and second parameters of user's context over a determined time period of a direct or indirect contact between portions of user's limbs and the one or more sensors; identifying, by the computing device, from the obtained readings of the first and second parameters, at least a first feature of the first parameter and a second feature of the second parameter that is temporally correlated with the first feature; and determining, by the computing device, a third parameter of the user's context based at least in part on the identified first and second features.

Example 21 may include the subject matter of Example 20, further comprising: identifying, by the computing device, a first plurality of features of the first parameter and a second plurality of features of the second parameter, wherein the first plurality of features includes the first feature and the second plurality of features includes the second feature; determining, by the computing device, empirical correlation between the first and second pluralities of features; and deriving, by the computing device, the third parameter based at least in part on the empirical correlation between the first and second pluralities of features.

Example 22 may include the subject matter of Example 21, wherein the user's context comprises user's physiological context and user's physiological state, wherein the first, second, and third parameters are related to the user's physiological context, and wherein the method further comprises: obtaining, by the computing device, readings indicating the user's physiological state, during the maintenance of the direct or indirect contact between the portions of user's limbs and the one or more sensors disposed on the work surface; and determining, by the computing device, boundary values of the third parameter for the user, based at least in part on the user's physiological state, wherein the portions of limbs include hands, palms, or wrists.

Example 23 is one or more non-transitory computing device-readable media having executable instructions for opportunistic measurements and processing of user's context stored thereon that, in response to execution, cause a computing device to: obtain, from one or more sensors disposed on a work surface of the computing device, readings of first and second parameters of user's context over a determined time period of a direct or indirect contact between portions of user's limbs and the one or more sensors; identify, from the obtained readings of the first and second parameters, at least a first feature of the first parameter and a second feature of the second parameter that is temporally correlated with the first feature; and determine a third parameter of the user's context based at least in part on the identified first and second features.

Example 24 may include the subject matter of Example 23, wherein the instructions further cause the computing device to: identify a first plurality of features of the first parameter and a second plurality of features of the second parameter, wherein the first plurality of features includes the first feature and the second plurality of features includes the second feature; determine empirical correlation between the first and second pluralities of features; and derive the third parameter based at least in part on the empirical correlation between the first and second pluralities of features.

Example 25 may include the subject matter of Example 24, wherein the instructions further cause the computing device to: obtain readings indicating user's physiological state, during the maintenance of the direct or indirect contact between the portions of user's limbs and the one or more sensors disposed on the work surface; and determine boundary values of the third parameter for the user, based at least in part on the user's physiological state, wherein the user's context comprises user's physiological context and the user's physiological state, wherein the first, second, and third parameters are related to the user's physiological context.

Example 26 is an apparatus for opportunistic measurements and processing of user's context, comprising: means for obtaining, from one or more sensors disposed on a work surface of the computing device, readings of first and second parameters of user's context over a determined time period of a direct or indirect contact between portions of user's limbs and the one or more sensors; means for identifying, from the obtained readings of the first and second parameters, at least a first feature of the first parameter and a second feature of the second parameter that is temporally correlated with the first feature; and means for determining a third parameter of the user's context based at least in part on the identified first and second features.

Example 27 may include the subject matter of Example 26, further comprising: means for identifying, by the computing device, a first plurality of features of the first parameter and a second plurality of features of the second parameter, wherein the first plurality of features includes the first feature and the second plurality of features includes the second feature; means for determining empirical correlation between the first and second pluralities of features; and means for deriving the third parameter based at least in part on the empirical correlation between the first and second pluralities of features.

Example 28 may include the subject matter of Example 27, wherein the user's context comprises user's physiological context and user's physiological state, wherein the first, second, and third parameters are related to the user's physiological context, and wherein the apparatus further comprises: means for obtaining readings indicating the user's physiological state, during the maintenance of the direct or indirect contact between the portions of user's limbs and the one or more sensors disposed on the work surface; and means for determining boundary values of the third parameter for the user, based at least in part on the user's physiological state, wherein the portions of limbs include hands, palms, or wrists.

Various operations are described as multiple discrete operations in turn, in a manner that is most helpful in understanding the claimed subject matter. However, the order of description should not be construed as to imply that these operations are necessarily order dependent. Embodiments of the present disclosure may be implemented into a system using any suitable hardware and/or software to configure as desired.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims and the equivalents thereof.

What is claimed is:

1. An apparatus, comprising:
    a work surface, including at least portions of one of: a keyboard, a bezel, or a back side of the apparatus, wherein the apparatus comprises one of a tablet computer or a smartphone;
    a plurality of sensors mounted on the portions of the work surface, adapted to maintain a contact with portions of user's limbs that are in contact or interact with the work surface in a process of interaction of the user's limbs with the apparatus, wherein the plurality of sensors include two or more electrodes to obtain readings of electrocardiographic (ECG) data, one or more optical sensors to provide photoplethysmographic (PPG) data, and one or more motion sensors to provide jitter data associated with the user, wherein the jitter data includes indications of a motion of the user's limbs in relation to the work surface of the apparatus; and a processing circuitry coupled with the plurality of sensors, wherein the processing circuitry includes a processor and a memory having instructions that, in response to execution by the processor, is to collect and process the readings of the ECG, PPG, and jitter data provided by respective ones of the plurality of sensors, wherein to process includes to: collect a set of values from the ECG and PPG readings, including at least readings that indicate a pulse transit time, an amplitude of a PPG curve of the PPG data, and upward and downward slopes of the PPG curve; determine blood pressure of the user from an empirical correlation between the pulse transit time, the amplitude of the PPG curve, and the upward and downward slopes of the PPG curve; determine boundary values for the blood pressure of the user, by applying a logistic regression model to the set of values, wherein the boundary values indicate a normal state of the user, wherein to determine boundary values includes to adjust the boundary values over a time period using the jitter data, wherein the jitter data below a threshold is to provide ground truth data for determination of the boundary values; and provide an indication of a probability of the user being in the normal state, including render for display on a display of the apparatus a notification of the normal state.

2. The apparatus of claim 1, wherein the ECG data includes an interval measured from a beginning of a P-wave to a peak of an S-wave of a QRS complex of the ECG data, the upward slope of the PPG curve comprises a slope between lowest and highest points in the PPG curve, the amplitude of the PPG curve comprises a peak in the curve, and the downward slope of the PPG curve comprises a slope between the highest point and a beginning of a next PPG curve.

3. The apparatus of claim 1, wherein the blood pressure comprises systolic blood pressure (SBP) data and diastolic blood pressure (DBP) data, wherein the processing circuitry is to derive the SBP data and the DBP data from application of a machine-learning algorithm to the ECG and PPG data.

4. The apparatus of claim 1, wherein the one or more motion sensors comprise at least a selected one of: a gyroscope or accelerometer.

5. The apparatus of claim 1, wherein the one or more optical sensors comprise at least one of a light emitting diode (LED) and photodetector.

6. The apparatus of claim 1, wherein the apparatus is a computing device, wherein the portions of the user's limbs include at least one of: wrists, palms, or hands that are disposed on the work surface to interact with the apparatus.

7. An apparatus, comprising:
a casing, having at least one work surface that includes a plurality of sensors disposed on the work surface adapted to maintain contact with portions of a user's limbs that are in contact or interact with the work surface, to obtain readings of electrocardiographic (ECG) data, photoplethysmographic (PPG) data, and jitter data associated with the user, wherein the work surface of the casing includes at least portions of one of: a keyboard, a bezel, or a back side of the apparatus, wherein the apparatus comprises one of a tablet computer or a smartphone, wherein the plurality of sensors include two or more electrodes to obtain the readings of ECG data, one or more optical sensors to provide the PPG data, and one or more motion sensors to provide the jitter data;

a processor communicatively coupled with the plurality of sensors; and a memory coupled with the processor and having instructions which, in response to execution by the processor, is to collect and process the readings of the ECG, PPG, and jitter data provided by the respective of the plurality of sensors, wherein to process includes to: access a set of values from the ECG and PPG readings, including at least readings that indicate a pulse transit time, an amplitude of a PPG curve of the PPG data, and upward and downward slopes of the PPG curve; determine blood pressure of the user from an empirical correlation between the pulse transit time, the amplitude of the PPG curve, and the upward and downward slopes of the PPG curve; determine boundary values for the blood pressure of the user, by applying a logistic regression model to the set of values, wherein the boundary values indicate a normal state of the user, wherein to determine boundary values includes to adjust the boundary values over a time period using the jitter data, wherein the jitter data below a threshold is to provide ground truth data for determination of the boundary values; and provide an indication of a probability of the user being in the normal state, including output for display on a display of the apparatus a notification of the normal state.

8. The apparatus of claim 7, further comprising a sensor aggregator coupled with the plurality of sensors, to power on the plurality of sensors and to pre-process the readings provided by the plurality of sensors.

9. The apparatus of claim 8, wherein the sensor aggregator, the processor, and the memory are integrated on a system on chip (SOC), wherein the apparatus further comprises one of: a laptop computer or a desktop computer.

10. A computer-implemented method, comprising:
obtaining, by a computing device, from a plurality of sensors disposed on a work surface of the computing device that comprises one of a tablet computer or a smartphone, readings of electrocardiographic (ECG) data, photoplethysmographic (PPG) data, and jitter data associated with a user, in response to a contact between portions of the user's limbs and the plurality of sensors, wherein the work surface includes at least portions of one of: a keyboard, a bezel, or a back side of an apparatus, wherein the plurality of sensors include two or more electrodes to obtain the readings of ECG data, one or more optical sensors to provide PPG data, and one or more motion sensors to provide jitter data, wherein obtaining includes collecting, by the computing device, a set of values from the ECG and PPG readings, including at least readings that indicate a pulse transit time, an amplitude of a PPG curve of the PPG data, and upward and downward slopes of the PPG curve;

identifying, by the computing device, blood pressure of the user, from an empirical correlation between the pulse transit time, the amplitude of the PPG curve, and the upward and downward slopes of the PPG curve;

determining, by the computing device, boundary values for the blood pressure of the user, wherein the boundary values indicate a normal state of the user; wherein determining includes: applying, by the computing device, a logistic regression model to the set of values, wherein the boundary values indicate a normal state of the user; and adjusting, by the computing device, the boundary values over a time period using the jitter data, wherein the jitter data below a threshold is to provide ground truth data for determining the boundary values; and providing, by the computing device, an indication of a probability of the user being in the normal state, including outputting a notification of the normal state on a display of the computing device.

11. The computer-implemented method of claim 10, wherein the ECG data includes an interval measured from a beginning of a wave to a peak of the wave of a QRS complex of the ECG data, the upward slope of the PPG curve comprises a slope between lowest and highest points in the PPG curve, the amplitude of the PPG curve comprises a peak in the curve, and the downward slope of the PPG curve comprises a slope between the highest point and a beginning of a next PPG curve.

12. One or more non-transitory computing device-readable media having executable instructions stored thereon that, in response to execution, cause a computing device to:

obtain, from a plurality of sensors disposed on a work surface of the computing device that comprises one of a tablet computer or a smartphone, readings of electrocardiographic (ECG) data, photoplethysmographic (PPG) data, and jitter data associated with a user, in response to a contact between portions of the user's limbs and the plurality of sensors, wherein the work surface includes at least portions of one of: a keyboard, a bezel, or a back side of the computing device, wherein the plurality of sensors include two or more electrodes to obtain the readings of ECG data, one or more optical sensors to provide PPG data, and one or more motion sensors to provide jitter data, wherein to obtain includes to collect a set of values from the ECG and PPG readings, including at least readings that indicate a pulse transit time, an amplitude of a PPG curve of the PPG data, and upward and downward slopes of the PPG curve;

identify blood pressure of the user, from an empirical correlation between the pulse transit time, the amplitude of the PPG curve, and the upward and downward slopes of the PPG curve;

determine boundary values for the blood pressure of the user, wherein the boundary values indicate a normal state of the user, wherein to determine includes to: apply a logistic regression model to the collected set of values, wherein the boundary values indicate a normal state of the user; and adjust the boundary values over a time period using the jitter data, wherein the jitter data below a threshold is to provide ground truth data for determining the boundary values; and provide an indication of a probability of the user being in the normal state, including render for display on a display of the computing device a notification of the normal state.

13. The non-transitory computing device-readable media of claim 12, wherein the ECG data includes an interval measured from a beginning of a wave to a peak of the wave of a QRS complex of the ECG data, the upward slope of the PPG curve comprises a slope between lowest and highest points in the PPG curve.

* * * * *